United States Patent
Yamazaki et al.

(10) Patent No.: US 9,599,631 B2
(45) Date of Patent: Mar. 21, 2017

(54) AUTOMATIC ANALYZER

(75) Inventors: Isao Yamazaki, Tokyo (JP); Masaharu Nishida, Tokyo (JP); Kumiko Kamihara, Tokyo (JP); Hideto Tamezane, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 14/239,379

(22) PCT Filed: Jul. 19, 2012

(86) PCT No.: PCT/JP2012/068380
§ 371 (c)(1),
(2), (4) Date: Feb. 28, 2014

(87) PCT Pub. No.: WO2013/031416
PCT Pub. Date: Mar. 7, 2013

(65) Prior Publication Data
US 2014/0220693 A1 Aug. 7, 2014

(30) Foreign Application Priority Data
Sep. 1, 2011 (JP) .................................. 2011-190664

(51) Int. Cl.
*G01N 35/10* (2006.01)
*G01N 35/00* (2006.01)

(52) U.S. Cl.
CPC ..... *G01N 35/1002* (2013.01); *G01N 35/1011* (2013.01); *G01N 35/1016* (2013.01);
(Continued)

(58) Field of Classification Search
CPC ........... G01N 35/1016; G01N 35/1011; G01N 35/1002; G01N 35/1009; G01N 35/10;
(Continued)

(56) References Cited

U.S. PATENT DOCUMENTS 5,540,081 A * 7/1996 Takeda ............... G01N 35/1016
340/626
2004/0034479 A1 2/2004 Shimase et al.
(Continued)

FOREIGN PATENT DOCUMENTS

EP 1209471 A2 5/2002
EP 1391734 A2 2/2004
(Continued)

OTHER PUBLICATIONS

International Preliminary Report on Patentability received in International Application No. PCT/JP2012/068380 dated Mar. 13, 2014.
(Continued)

*Primary Examiner* — Christine T Mui
(74) *Attorney, Agent, or Firm* — Mattingly & Malur, PC

(57) ABSTRACT

A plunger is moved downwardly in predetermined distance while the tip of the sample probe is immersed in a sample to suck the sample into the probe. A pressure sensor detects the pressure fluctuation during the suction operation, an AD converter converting the signals into digital signals to send the signals for a signal processing unit. The signal processing unit extracts feature variables data of a suction waveform to calculate the Statistical distance from normal group data. The Statistical distance an a threshold value are compared with each other, it is judged that there is an abnormality in the suction operation when the Statistical distance is more than or equal to the threshold value. When the Statistical distance is smaller than the threshold value, an operation is proceeded to a discharge operation.

14 Claims, 7 Drawing Sheets

(52) U.S. Cl.
CPC ............... *G01N 2035/1018* (2013.01); *G01N 2035/1062* (2013.01); *Y10T 436/119163* (2015.01)

(58) Field of Classification Search
CPC ........... G01N 35/00; G01N 2035/1018; G01N 2035/1062; G01N 2035/1048; G01N 2035/1027; Y10T 436/119163; Y10T 436/11; Y10T 436/00
USPC .................... 436/54, 43; 422/81, 68.1, 50
See application file for complete search history.

(56) References Cited

U.S. PATENT DOCUMENTS

| | | |
|---|---|---|
| 2010/0327012 A1 | 12/2010 | Saegusa |
| 2011/0174343 A1 | 7/2011 | Azuma et al. |

FOREIGN PATENT DOCUMENTS

| | | | |
|---|---|---|---|
| JP | 2004-125780 A | | 4/2004 |
| JP | 2006-300814 A | | 11/2006 |
| JP | 2009-210351 A | | 9/2009 |
| JP | 2009-210352 A | | 9/2009 |
| JP | 2012-026942 A | | 2/2012 |
| WO | 2010/038546 A1 | | 4/2010 |

OTHER PUBLICATIONS

Extended European Search Report received in corresponding European Application No. 12828882.6 dated Mar. 25, 2015.

\* cited by examiner

AUTOMATIC ANALYZER

TECHNICAL FIELD

The present invention relates to an automatic analyzer analyzing components of blood or the like automatically.

BACKGROUND ART

An automatic analyzer dispenses samples composed of biological samples, such as blood, urine or the like into reaction containers on a reaction line from sample containers, further dispensing reagents into the reaction containers on the reaction line from reagent containers, measuring mixed solutions of samples and reagents by using a measurement device such as a photometer to execute qualification analysis or quantitative analysis.

A tip of a dispensing probe is immersed into solution to be dispensed at the dispensing operations of sample and reagent, the quantities of the solution attached to the outer wall of the probe becomes large in proportion to the immersion depth of the probe into the solution, so that the quantities of contamination to the probe becomes large.

Accordingly, in order to reduce the immersion depth of the dispensing probe into the solution to the utmost, the motion of the probe is controlled generally as follows. The surface of the solution in the container is detected, the down movement of the probe being stopped when the tip of the probe reaches to the position which is slightly downward from the surface of the solution. Subsequently, a predetermined quantity of the solution is sucked into the probe. A Method for measuring the electrical static capacitance between the dispensing probe and the solution to be dispensed is used as means for detecting the surface of the solution to be dispensed. In this method, the surface of the solution is detected by using the very large change of the electrical static capacitance at the time when the dispensing probe contacts to the solution to be dispensed.

At the dispensing operation using a dispensing probe, a predetermined quantity of liquid may not be dispensed correctly because of a liquid surface detection failure caused by bubbles or the like on the liquid to be dispensed, solid materials in the liquid to be dispensed, or the like. This means that the reliability of an automatic analyzer is damaged largely.

Large numerous automatic analyzers are suggested as means for solving the above deficiency, each of the automatic analyzer including a pressure sensor installed in a dispensing flow passage including a sample probe in order to detect a clogging condition or the like of the sample probe on the basis of the fluctuation of the pressure.

The patent document 1 discloses the technique for detecting an abnormal of suction operation on the basis of the Mahalanobis distance calculated from the reference data made by time series data of pressures at normal sucking operations and the comparison data of time series data of the output values from the pressure sensor at sucking operations.

According to the patent document 1, the reference data are prepared in accordance with the dispensing conditions including the quantity of the liquid to be dispensed, and an abnormal condition can be detected correctly at different dispensing conditions. Further, abnormal conditions are detected by calculating the Mahalanobis distance on the basis of the time series data of pressures of all intervals from the start to the end of the suction operation, so that not only an abnormal condition caused by the specific cause but also abnormal conditions caused by various causes can be detected.

PRIOR ART DOCUMENTS

Patent Document

Patent Document 1: JP2004-125780A

SUMMARY OF THE INVENTION

Problem to be Solved by the Invention

According to the method described in the patent document 1, however, the apparatus must store the reference data of the pressure waveform at the normal dispending operation, so that the reference data must be prepared independently for each quantity of liquid to be dispensed in order to detect an abnormal condition with high accuracy, and great amount of reference data are required if the kinds of the quantities of the liquid processed by the apparatus. Therefore, there are problems that many times are required to prepare the reference data, and the storage area must be for great amount of reference data.

An object of the present invention is to realize an automatic analyzer and a method for judging normal and abnormal of the dispensing operation for detecting abnormal condition of dispensing operation caused by various causes to execute an analysis with high reliability with no requirement of great amount of reference data.

Means for Solving the Problems

For attaining the foregoing object, the present invention is configured as described below.

An automatic analyzer and a method for judging normal and abnormal of the dispensing operation according to the present invention comprise a dispensing mechanism including a dispensing probe for dispensing samples or reagents into reaction containers, and an analysis unit for analyzing samples in the reaction containers, calculating the Statistical distance between the pressure data at the plural times in the dispensing probe at the dispensing operation of the dispensing probe and the predetermined reference pressure change data, judging whether or not the calculated Statistical distance is lower than a constant threshold value, so that the automatic analyzer and a method judge whether or not the dispensing operation of the dispensing probe is executed normally.

Effects of the Invention

It can be realized that an automatic analyzer and a method for judging normal and abnormal of the dispensing operation detect abnormal condition of dispensing operation caused by various causes to execute an analysis with high reliability with no requirement of great amount of reference data.

MODE FOR CARRYING OUT THE INVENTION

The mode for carrying out the present invention will be described herein under with reference to the drawings.
Embodiments
(The Embodiment 1)

Figure 1:
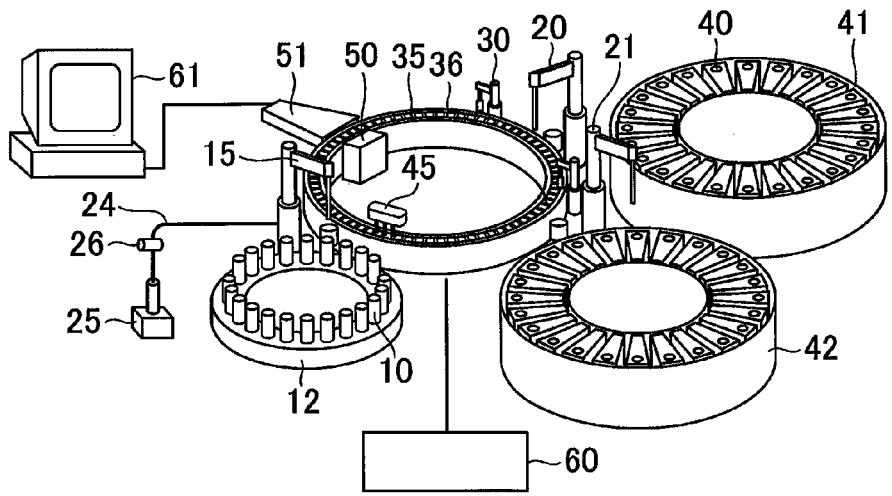
FIG. 1 is a schematic construction drawing of an automatic analyzer to which the present invention is applied.
Figure 2:
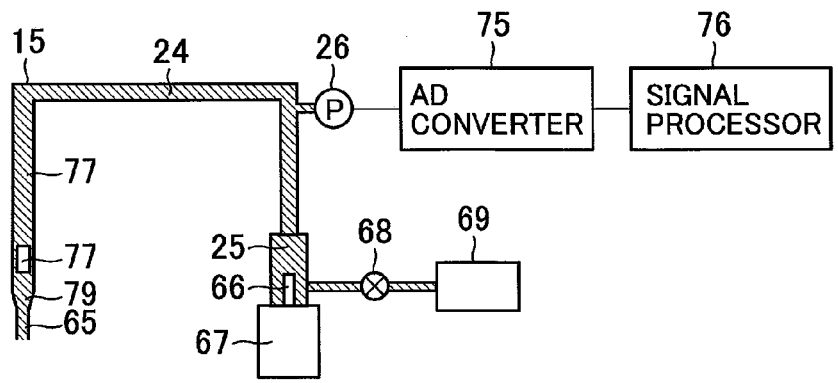
FIG. 2 is a drawing for explaining the main part (probe pressure signal processing unit) in the first embodiment of the present invention.

FIG. 1 is a schematic construction drawing of an automatic analyzer to which the present invention is applied, FIG. 2 being a drawing for explaining the main part (probe pressure signal processing unit) in the first embodiment of the present invention.

In FIG. 1, the automatic analyzer includes a sample disk 12 capable for loading a plurality of sample containers 10 for holding samples, the first reagent disk 41 and the second reagent disk 42 capable for loading a plurality of reagent containers 40 for holding reagents, and a reaction disk 36 on which a plurality of reaction containers 35 are arranged at its circumference.

Further, the automatic analyzer includes a sample probe 15 for dispensing a sample sucked from the sample container 10 into the reaction container 35, the first reagent probe 20 for dispensing the reagent sucked from the reagent container 40 in the first reagent disk 41 into the reaction container 35, the second reagent probe 21 dispensing the reagent sucked from the reagent container 40 in the second reagent disk 42 into the reaction container 35, the mixing device 30 for mixing the liquid in the reaction container 35, the container washing mechanism 45 for washing the reaction container 35, the light source 50 set on the vicinity of the periphery of the reaction disk 36, the spectrometer 51, the computer 61 connected to the spectrometer 51, and the controller 60 for controlling the operations of the automatic analyzer entirely and for executing the data exchanging operation to an outer units.

The sample probe 15 is connected to the quantitative pump 25 through the dispensing flow passage 24, the pressure sensor 26 being installed in the middle portion of the dispensing flow passage 24. A dispensing flow passage, a quantitative pump, and a pressure sensor, which are not shown in FIG. 1, are connected to the first reagent probe 20 and the second reagent probe 21 in similar to the sample probe 15.

As shown in FIG. 2 in detail, the reduction part 65 having small sectional area is formed in the tip end of the sample probe 15. Further, the plunger 66 driven by the drive mechanism 67 is arranged on the quantitative pump 25. The quantitative pump 25 is connected to the pump 69 through the valve 69. The pressure sensor 26 is connected to the signal processor (the signal processing unit) 76 through the AD converter 75. The sample probe 15 includes a movement mechanism (not shown), being able to move in vertical direction and to rotate so that the sample probe can move to the sample container 10 and reaction container 35.

The apparatus according to the present embodiment operates as described below.

The sample such as blood to be inspected is received in the sample container 10 which is set on the sample disk 12. The kinds of the analysis required for each sample are inputted into the controller 60. The predetermined amount of the sample extracted by the sample probe 15 from the sample container 10 is dispensed into the reaction containers 35 arranged on the reaction disk 36. The predetermined amount of the reagent is dispensed into the reaction container 35 from the reagent container 40 set on the reagent disk 41 or 42 by the reagent probe 20 or 21, the liquid in the reaction container 35 being mixed by the mixing device 30. The dispensing amounts of the sample and reagent are previously determined for each of the kinds of analysis.

The reaction disk 36 frequently rotates and stops periodically, the photometry operation is executed by the spectrometer 51 at the timing that the reaction container 35 passes to the front of the light source 50. The photometry operations are repeated during the reaction time of 10 minutes, thereafter, the reaction solution in the reaction container 35 being discharged by the container washing mechanism 45, and the reaction container 35 being washed by the container washing mechanism 45. Meanwhile, operations using other samples and reagents in other reaction containers 35 are executed in parallel. The photometry data detected by the spectrometer 51 is calculated by the computer 61 to obtain the concentration of the components for each kind of analysis, and the concentration of the components are displayed on the display of the computer 61.

The operation of the sample probe 15 will be described in detail with reference to FIG. 2.

Firstly, the controller 60 opens and closes the valve 68 to fill the inner portion of the flow passage of the sample probe 15 with the system liquid 77 supplied from the pump 69. Next, the controller 60 moves the plunger 66 downwardly by using the drive mechanism 67 in condition that the tip of the sample probe 15 is in the air, the separate air 78 being sucked into the sample probe 15.

Next, the controller 60 moves the sample probe 15 downwardly into the sample container 10, moving the plunger 66 downwardly with predetermined distance to suck the sample into the probe in condition that the tip of the probe 15 immersed in the sample. In this case, the suction solution 79 is the sample. The fluctuation of the pressure in operations succeeding from the sucking operation is detected by the pressure sensor 26, the detected fluctuation of the pressure being converted into digital signals by the AD converter, the digital signals being transferred to the signal processor 76. Thereafter, the sample probe 15 is moved above the reaction container 35, discharging the sample into the reaction container 35.

The pressure sensor 26 detects the fluctuation of the pressure again during the operations succeeding from the discharging operation, the detected fluctuation of the pressure being converted into the digital signals by the AD converter 75, the digital signals being transferred to the signal processor 76. Subsequently, the inner and outer portions of the sample probe 15 are washed by operating the open and close of the valve 68 to prepare the sample probe 15 for next analysis operation.

The signal processor 76 judges the presence or absence of an abnormal discharging operation on the basis of the pressure waveforms of the suction operation and the discharging operation, stopping the analysis operation, an alarm being displayed, the return operation being executed when the signal processor 76 judges that there was an abnormal operation. The return operation is selected one of the operations of the removing the cause of the abnormal to execute the discharging operation again, the execution of inspection of other sample, the stop of the apparatus, or the like.

Figure 3:
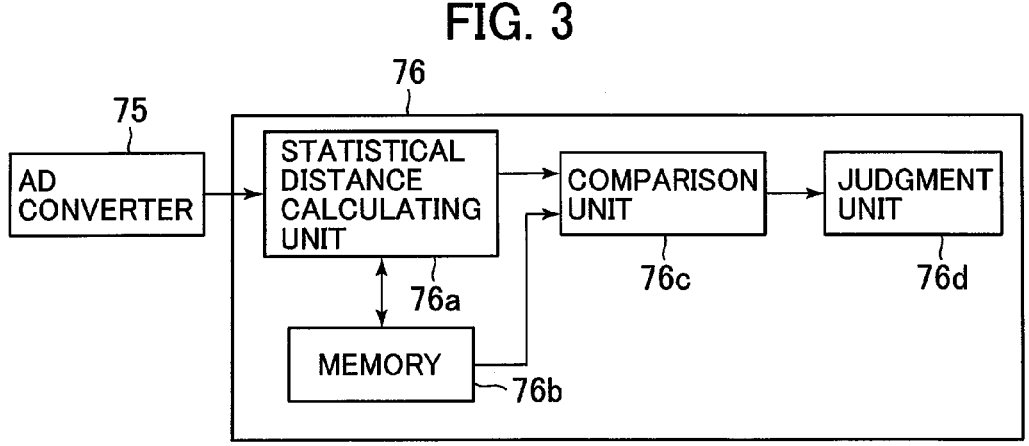
FIG. 3 is a drawing of inner construction of a signal processor.

FIG. 3 is a drawing of inner construction of the signal processor 76. The signal processor 76 includes the statistical distance calculating unit 76a, the memory 76b, the comparison unit 76c, and the judgment unit 76d.

The judgment unit 76 of the signal processor 76 transmits the judgment result to the controller 60. The signal processor 76 may be installed in independent of the controller 60, and the signal processor 76 may arranged in the controller 60.

Figure 4:
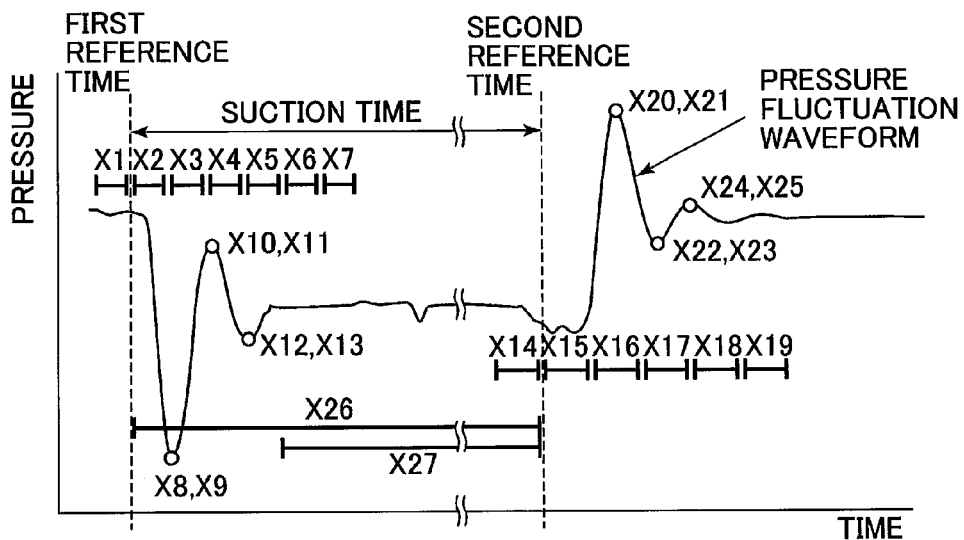
FIG. 4 is a graph showing the feature variables in the first embodiment of the present invention.

The detail of the judgment of the presence or absence of abnormal dispensing operation will be described with reference to FIG. 3, the judgment being executed by the signal processor 76. FIG. 4 is a graph showing the fluctuation waveform of the pressure detected by the pressure sensor 26 before and after the sucking operation, the horizontal axis representing times, the vertical axis representing pressures. The curve shown in FIG. 4 is the pressure fluctuation waveform.

The suction time is the time during the down movement of the plunger 66, the sample being sucked into the tip of the sample probe 15. As shown in FIG. 4, the pressure in the sample probe 15 is lowered during the suction operation time, being increased after the suction operation to return the value as same as the value before the suction operation, the pressure values being fluctuated at the start of the suction operation and the stop of the suction operation.

Reference numerals X1 to X27 shown in FIG. 4 are the feature variables. In one embodiment of the present invention, the suction operation start time is the first reference time, the average values of the pressures at the constant time interval before and after the first reference time are represented by X1 to X7. The first local minimum of the pressure value after the first reference time is represented by X8, the timing of the first local minimum being represented by X9, the first local maximum of the pressure value after the first reference time being represented by X10, the timing of the first local maximum being represented by X11, the second local minimum of the pressure value after the first reference time being represented by X12, the timing of the second local minimum being represented by X13.

Further, the suction operation ended time is the second reference time, the average values of the pressures at the constant time interval before and after the second reference time are represented by X14 to X19. The first local maximum of the pressure value after the second reference time is represented by X20, the timing of the first local maximum being represented by X21, the first local minimum of the pressure value after the second reference time being represented by X22, the timing of the first local minimum being represented by X23, the second local maximum of the pressure value after the second reference time being represented by X24, the timing of the second local maximum being represented by X25.

Further, the average value of the pressure during the sucking operation time is represented by X26, RMS value of the one part of the pressure of the sucking operation time.

In the signal processor 76, the statistical distance calculation unit 76a calculates the feature values X1 to X27 with respect to the digital signals of the pressure waveforms transmitted from the AD converter 75. Further, the signal processor 76 holds the normal group data of the results of the feature values X1 to X27 in case that the sample probe 15 could dispense the samples normally, the normal group data being stored in the inner memory 76b, the statistical distance calculation unit 76a calculating the statistical distance s D from the normal group data of the calculated feature values X1 to x27. Further, the comparison unit 76c compares the statistical distance s D with the predetermined threshold values stored in the memory 76b, supplying the difference the threshold values and the statistical distance s D to the judgment unit 76d. The judgment unit 76d judges that the abnormal sucking operation was happened when the difference between the statistical distance D and the threshold value is large, judging that the sucking operation was executed normally when the difference is small.

The processes as same as the above-mentioned processes of the sucking operation are executed for the discharging operation, the judgment unit 76d judging whether or not the discharging operation was executed normally.

The statistical distance D is the index mark which is numeric conversion of the similarity between two events represented by plural feature values, being the calculation how long the measured data at its time from the collection of the normal data group in case of tone embodiment of the present invention. There are numerous kinds of the calculation methods as the statistical distance D, such as the Mahalanobis distance, the Euclidean distance, Chebychev distance, the Multi variate normal density, the Minkowski distance, or the like. In this case, the statistical distance D is calculated by using the following equations (1) and (2).

$$u_i = (X_i - \mu_i)/\sigma_i \quad (1)$$

$$D = u R^{-1} u' \quad (2)$$

In the above equations (1) and (2), the characters R, μ and σ represent correlation matrix, average vector, standard deviation of the normal data group respectively, the subscript i representing the factor of the number i. Further, the character D represents the Mahalanobis distance. Further, the character $u_i$ represents the normalized feature value, the character u representing the vector having the factor $u_i$. The character u' represents the transported vector of the u.

Next, the example of the judgment operation of the present embodiment will be described with reference to FIGS. 5 to 10.

Figure 5:
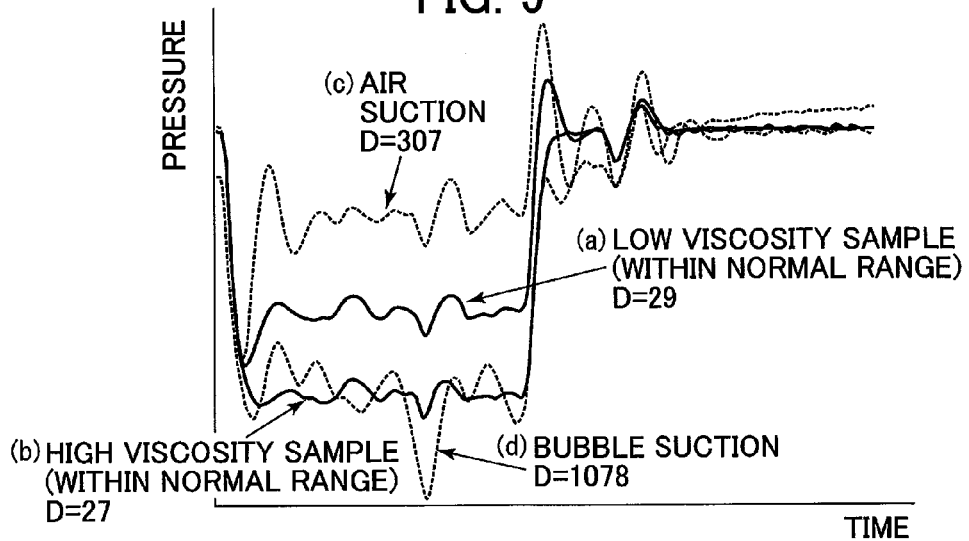
FIG. 5 is a graph showing examples of suction waveforms in the first embodiment of the present invention.

FIG. 5 shows the example for judging the suction of the sample. The waveforms (a) and (b) are waveforms of a low viscosity sample and a high viscosity sample within the normal range, the calculated Statistical distance D of the waveforms being lower than or equal to 30 (D=29 in the case (a), D=27 in the case (b)).

The waveform (c) is the waveform in case that the sample probe 15 did not reach to the sample and the sample probe 15 sucked the air (air suction (D=307)). The waveform (d) is the waveform in case that the sample probe 15 sucked the part of bubble in condition that there were bubbles on the upper portion of the sample (bubble suction (D=1078)). In this case, the abnormal judgment threshold value is set about 100 (taking count of three times value of the Standard Deviation μ), so that the waveforms (a) and (b) are judged to be normal, and the waveforms (c) and (d) are judged to be abnormal.

Figure 6:
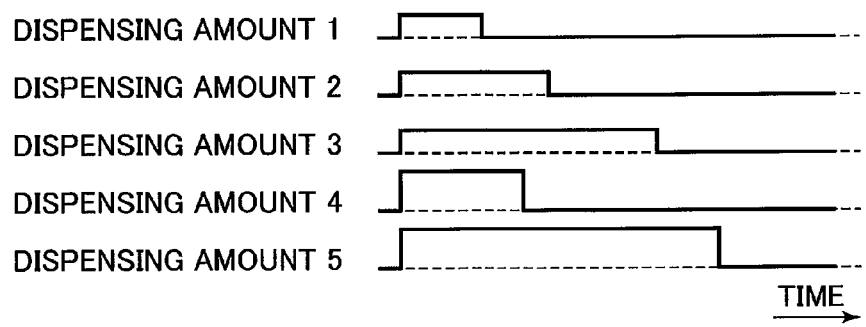
FIG. 6 is a drawing for explaining the relationship between the dispensing amount and the drive patterns in the first embodiment of the present invention.

FIG. 6 shows the driving patterns of the drive mechanism 67 of the reagent dispensing amount in case of the typical kind of the analysis processed by the present embodiment. The horizontal axis represents time, the vertical axis representing the movement speed of the plunger 66. The speeds of the dispensing amounts 1, 2, and 3 are equal with each other, being small. The speeds of the dispensing amounts 4 and 5 are equal with each other, being large. As shown in FIG. 6, the suction time and suction speed are varied greatly by difference of the dispensing amount.

Figure 7:
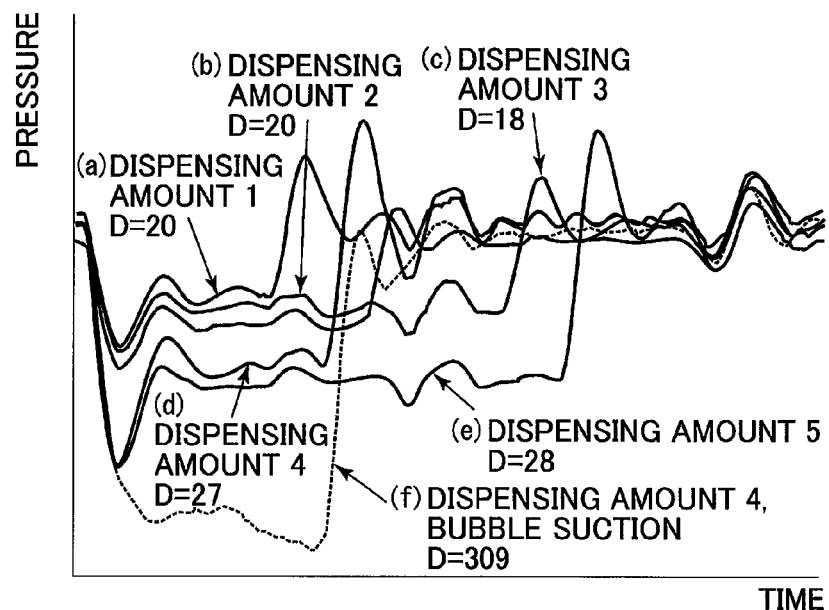
FIG. 7 shows the pressure waveforms in the probe in case that the amount of the liquid shown in FIG. 6 is sucked.

FIG. 7 is the drawing to show the pressure waveforms in the probe 15 in case that the dispensing amounts shown in FIG. 6 are sucked. In FIG. 7, the waveforms (a) to (e) are waveforms that the dispensing amounts 1 to 5 are sucked normally. The fluctuation time and amount of pressure are varied greatly by the difference of the driving patterns of the drive mechanism 67 for dispensing amounts. The normal group data to be compared are common in case that the fluctuation times and amounts of the pressure are greatly different, the calculated Statistical distance s D of the waveforms (a) to (e) being lower than or equal to 30 (D=18 to 28).

The (f) of FIG. 7 represents the waveform in case that the air is sucked at the condition of the dispensing amount 4. The calculated Statistical distance is 309. The threshold vale is set about 100, so that the waveforms (a) to (e) can be judged to be normal, and the waveform (f) can be judged to be abnormal. It is possible to judge correctly whether the normal suction or abnormal suction is executed.

As described above, if the conditions of the suction patterns are different with each other, it can be correctly judged whether an abnormal or a normal suction operation is executed, because the feature variables based on the first reference time (at the start of the suction operation) and the feature variables based on the second reference time (at the end of the suction operation) are used, and the suitable features can be extracted even if the conditions of the suction times are different with each other.

Figure 8:
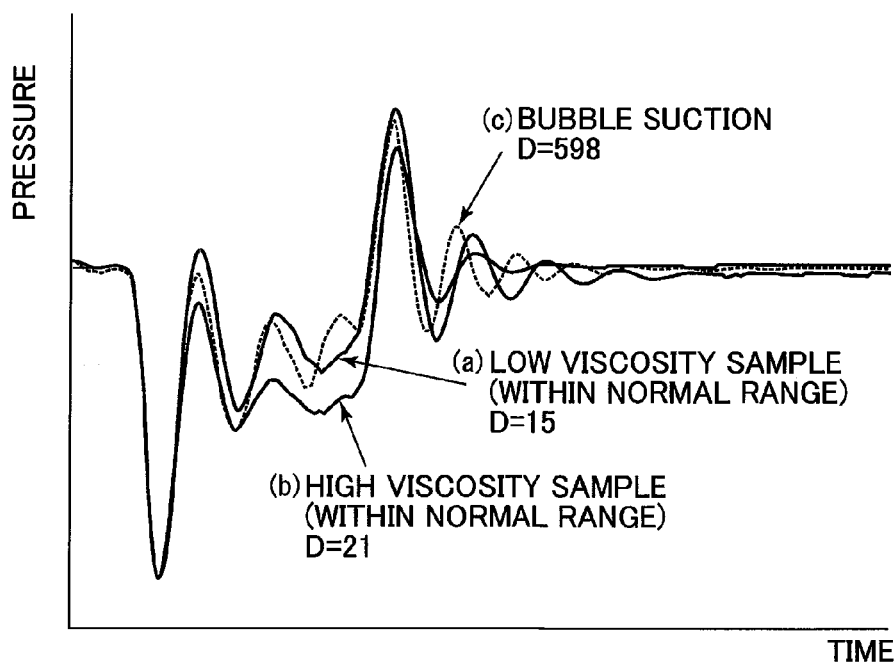
FIG. 8 shows the pressure waveforms of the reagent sucking operation in the reagent dispensing probe of the first embodiment of the present invention.

FIG. 8 is the drawing to show the pressure waveforms of the first reagent dispensing probe 20 at the reagent suction operation. The dispensing amount of the reagent is large in comparison with that of the sample, so that the reduction part 65 of the tip of the reagent dispensing probe 20 is thick in comparison with that of the sample probe 15. Therefore, the effect of the difference between the viscosities of the fluid to be sucked is small against to the pressure waveforms.

In this embodiment, as shown in FIG. 8, the Statistical distance s D of the normal suction waveforms (a) and (b) are 15 and 21 which are lower than or equal to 30. If the bubble is sucked into the probe, the Statistic Distance D of the waveform (c) is 598 which is large value. It can be correctly judged that an abnormal is presence or absence, when the threshold value is set about 100.

As described above, an abnormal operation can be judged even if there is small difference of the pressure in the waveform because the pressure values and timings of the maximum and the minimum values of the fluctuation waveform at both of the suction start time and end time are picked up as feature values. If the difference of the pressure losses at the reduction part 65 of the tip of the probe is small, the amount of air in the probe increases when a bubble is sucked into the probe, and the characteristics of the fluctuation is differ from that of a normal operation, and the timing of the extremal value of the fluctuation is drifted from that of a normal operation, and the method of present embodiment can detect the drift of the timing of the extremal value.

Figure 9:
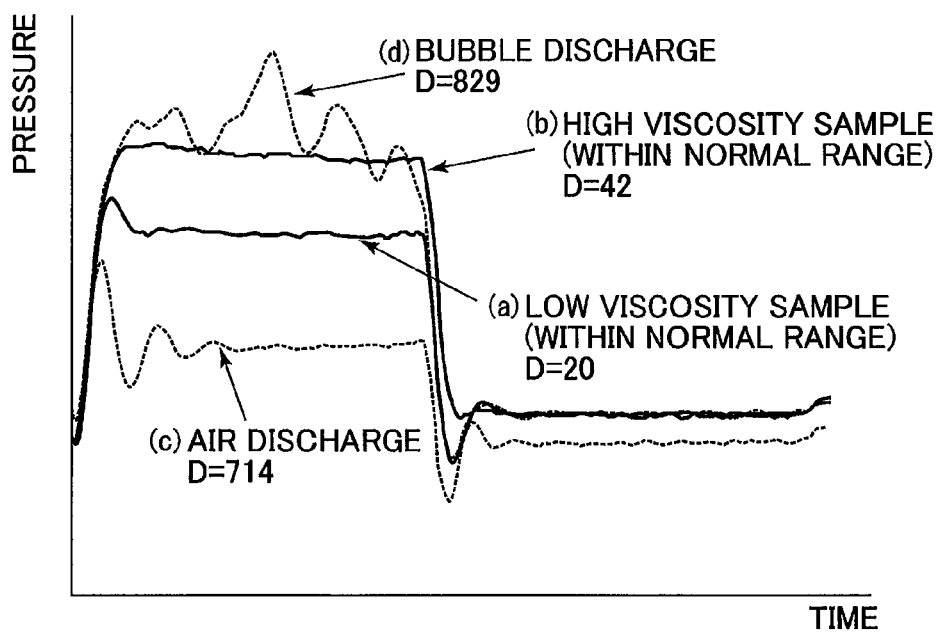
FIG. 9 shows the pressure waveforms of the sample discharging operation in the sample probe of the first embodiment of the present invention.

FIG. 9 is the drawing to show the pressure waveform of the discharging operation of the sample probe 15. In FIG. 9, the pressure increases during the sample discharging operation, it being a revers condition against the sample suction operation, and the pressure value returning to the pressure value before the discharging operation after the end of the sample discharging operation. There are fluctuation waveforms of the pressure at the start and the end of the discharging operation, these fluctuations being smaller than the fluctuation of the suction operation.

In FIG. 9, the waveforms (a) and (b) represent the cases of the low viscosity and the high viscosity samples both of which are within the normal range, the Statistical distance D of the waveform (a) being 20, the Statistical distance D of the waveform (b) being 42, the both distances being lower than or equal to 50. The waveform (c) is the pressure waveform of the discharging operation in case that the probe sucked the air, the Statistical distance D being 714. The waveform (d) is the waveform of the discharging operation in case that the probe sucked the bubble with the sample, the Statistical distance D being 829. Also in this case, it can be correctly judged that an abnormal is presence or absence, when the threshold value is set about 100.

Figure 10:
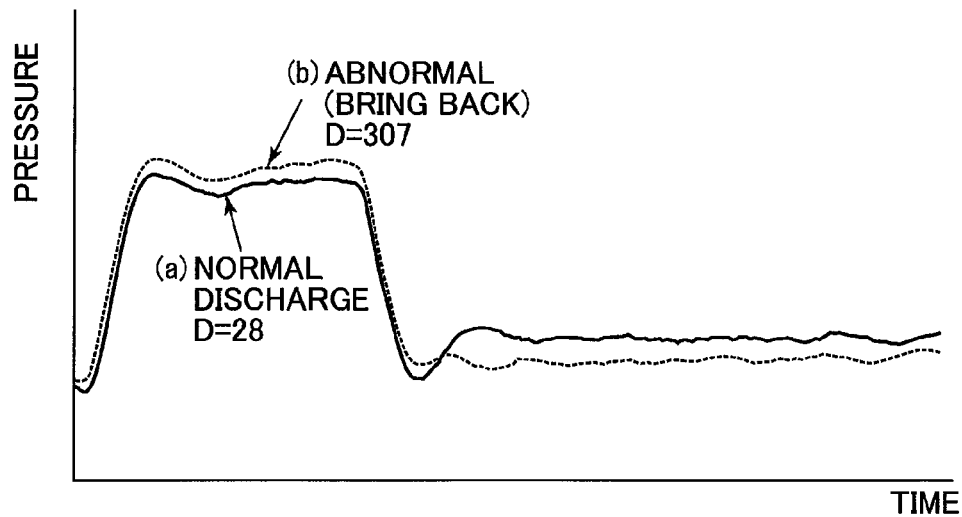
FIG. 10 shows the pressure waveforms of the sample discharging operation in the sample probe of the first embodiment of the present invention.

FIG. 10 is the drawing to show other pressure waveforms at the discharging operation of the sample probe 15. In FIG. 10, the waveform (a) is the waveform in case that the dispensing operation can be executed normally, the Statistical distance D being 28. The waveform (b) is the waveform in case that one part of the droplet of the sample is attached to the tip of the sample probe 15 after the sample discharging operation. In case of the waveform (b), since the sample probe 15 brings back the attached sample, the amount of the discharge being shortened. Also in this case, the Statistical distance D is 307 which is large, so that this case can be discriminated from a normal operation.

Since the normal group data, which have only normal waveforms, are used, the feature variables based on the end time of the discharging operation being used, so that the features of the waveforms after the end of the discharging operation are taken accurately. Therefore, an abnormal, whose waveform slightly different from a normal waveform, can be correctly discriminated.

Figure 11:
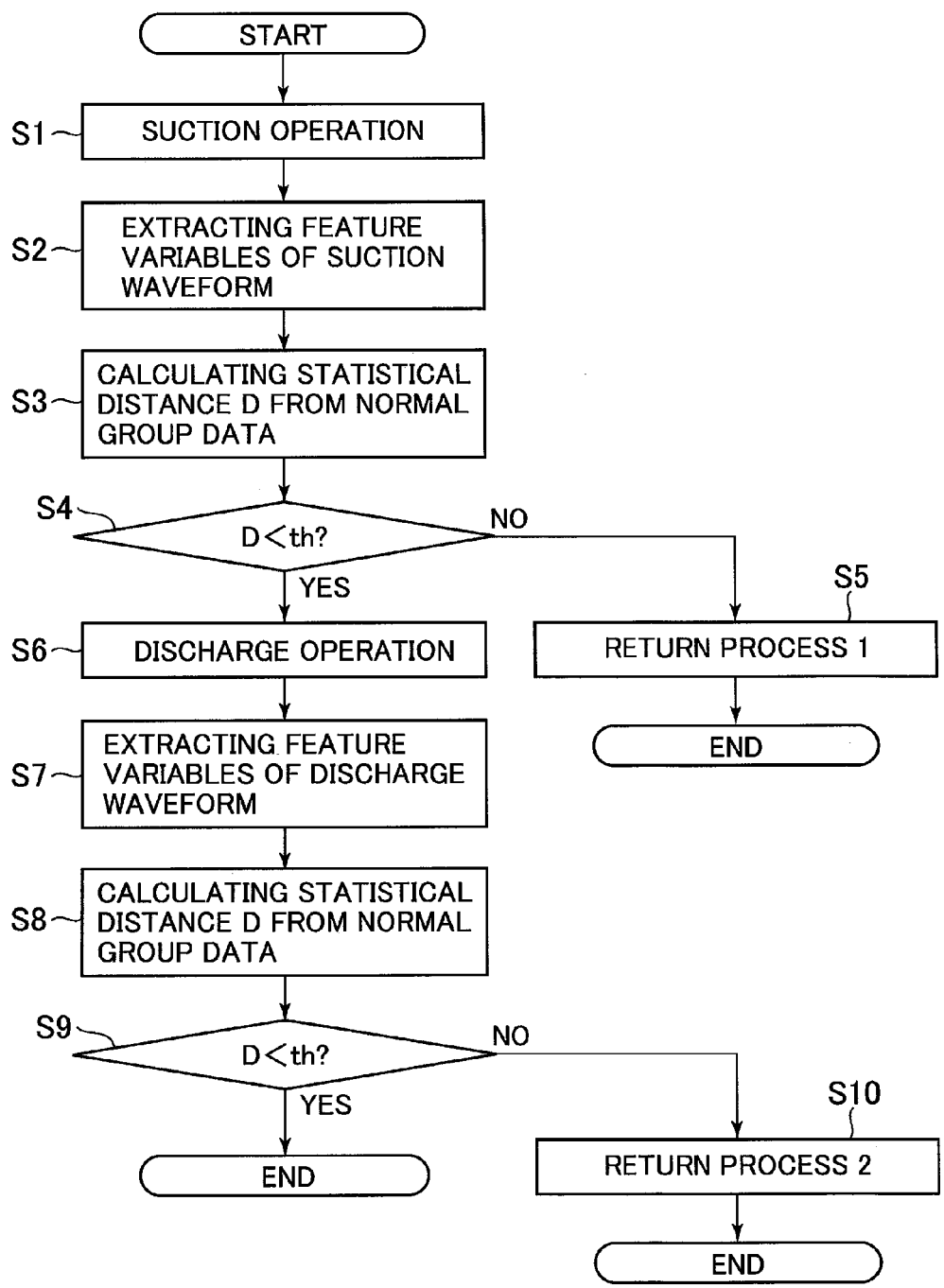
FIG. 11 is a flowchart of the judgment operation in the first embodiment of the present invention.

FIG. 11 is the flow chart of the discriminating operation of the present embodiment.

In FIG. 11, the sample probe 15 executes the suction operation (the step S1), the statistical process calculation unit 76a extracting the values of the feature variables of the suction waveforms, the statistical process calculation unit 76a calculating the Statistical distance D from the normal group data stored in the memory 76b (the steps S2 and S3). The Statistical distance D is compared with the threshold value th stored in the memory 76b by the comparison unit 76v, the results being supplied to the judgment unit 76d (the step S4).

The judgment unit 76d judges that there is abnormal suction operation, executing the return process 1 (the step S5), when the Statistical distance D is more than or equal to the predetermined threshold value th. In the return process 1, the judgment unit 76d transmits the abnormal suction operation to the controller 60 and the computer 61, the operations of the alarm process and the proceeding the process for the next sample being executed by the control operations of the controller 60 and the computer 61.

When the Statistical distance D is smaller than the threshold value th, the process being proceeded to the discharge operation by the control of the controller 60 in accordance with the instruction from the judgment unit 76*d* (the step S6). After the discharge operation, the feature variables of the discharge waveform are extracted, the Statistical distance s D from the normal group data being calculated (the steps S7 and S8). Further, when the Statistical distance D is more than the predetermined threshold value th, it is judged that there is an abnormal in the discharge operation (the step S9), the return operation 2 being executed (the step S10). In the return operation 2, the judgment unit 76*d* transmits the presence of the abnormal of discharge operation to the controller 60 and the computer 61, the alarm process and the analysis operation of the sample being not executed, the operation for washing the reaction containers used for the sample being executed by the control of the controller 60 and the computer 61.

When the Statistical distance D is smaller than the threshold value th, it is judged that there is no abnormality in the discharge operation, the discrimination operation being finished.

As described above, according to the present embodiment 1, the average of the pressure values, the maximum pressure value, the minimum pressure value, and their timings are took in as the feature variables at the constant timings based on the plunger operation start timing and the end timing as the first reference timing and the second reference timing respectively from the pressure fluctuation at the sample suction and discharge operation of the sample probe 15, the Statistical distance s D from the normal group data being compared with the threshold value. Therefore, it can be detected with good sensitivity for the pressure fluctuation in the dispensing operation that there is the feature of pressure fluctuation different from the feature of the pressure fluctuation at the normal dispensing operation, and an abnormality at the dispensing operation can be judged, and an overlooked failure at the dispensing operation can be prevented, and the output operation of an erroneous analysis result can be prevented, so that an automatic analyzer capable for analyzing operation with high reliability can be provided.

Further, in the present embodiment 1, the Statistical distance s D from the normal group data calculated by using the plural feature variables are compared with one threshold value th, it is the simple logic to judge the present or absence of an abnormality, so that it is not required that the pressure values at plural times of the waveform are compared with the plural pressure values of the normal data respectively, that is to compare the complicated judgment references, and the abnormalities of dispensing operation generated by various causes can be detected without the overlook of an abnormality. Therefore, an automatic analyzer capable for correctly discriminating the presence or absence of an abnormality with a simple calculation and high reliability can be provided.

Further, in the present embodiment 1, the normal group data obtained from the liquid within the range of viscosity which can be obtained from a normal sample is used, so that the apparatus can detect the plural dispensing abnormalities caused by the air suction, the bubble suction, a sample having high viscosity without a normal range, the happening of clogging by a solid material in the sample, or the like.

Therefore, an automatic analyzer capable for analyzing operation with high reliability can be provided.

Further, in the present embodiment 1, small number of the feature variables is extracted from the time series of pressure fluctuation to calculate the Statistical distance for the feature variables, so that the calculation amount required to calculate the Statistical distance can be reduced, and the high speed discrimination can be processed with processing operations for abnormalities caused by various kinds of causes, and an automatic analyzer capable for executing an analysis with high performance and high reliability can be provided.

Further, in the present embodiment 1, the apparatus uses the feature variables based on the plunger operation starting time at the suction operation or the discharge operation and the feature variables base on the end time of the plunger operation, so that an abnormality can be discriminated correctly by using the normal group data which is used commonly for the dispensing operations of different conditions of operation time, the operation speed, or the like of the plunger. Therefore, the number of the normal group data can be reduced, and the process for discriminating can be simplified even when the apparatus executes various kinds of analyses having dispensing conditions which are different with each other. Accordingly, an automatic analyzer capable for executing a high reliability analysis with processing the various kinds of analysis conditions can be provided.

Further, the normal group data is commonly used for different dispensing operations having different conditions of operation times, operation speeds or the like, so that the normal group data having dispersion can be made. In order to prevent an error judgment for judging a normal operation as an abnormal operation, data having large dispersion within a normal range is required to be included into normal group data, and the data having large dispersion can be included into the normal range by making plural dispensing conditions as the common normal group data even when the number of normal group data is small, the labor for collecting the normal group data can be simplified, so that an automatic analyzer capable for correctly discriminating an abnormality by using small amount of normal group data with high accuracy and high reliability can be provided.

Further, in the present embodiment 1, since the pressure values and timings of the maximum point and the minimum point are extracted and used as the feature variables for calculating the Statistical distance, the discrimination of an abnormality can be accurately executed in condition that the discrimination operation is difficult to compare the pressure values at time intervals with each other such as a reagent dispensing system using a probe having thick inner diameter of tip of a probe, so that an automatic analyzer capable for detecting an abnormality in the sample dispensing operation and the reagent dispensing operation with high reliability can be provided.

Further, in the present embodiment 1, since the apparatus discriminates presence or absence of an abnormality in the both of the suction operation and the discharge operation, all abnormalities generated in the suction operation and the discharge operation can be discriminated without overlooking, so that an automatic analyzer capable for executing an analysis with high reliability can be provided.

Further, in the present embodiment 1, the abnormality of the suction waveform is discriminated at the end of the suction operation, and the recovery operation is executed when the abnormality is discriminated, so that there is a merit for executing the recovery operation before the start of the discharging operation. For example, if the discharging operation into the reaction container 35 is executed in condition that air or bubble is sucked into the probe, the bubble is discharged into the reaction container 35, and it is difficult to wash the reaction container 35. When the abnormality is detected in the sucking operation, the recovery operation is executed, and the discharge operation into the reaction container 35 is stooped at the recovery operation, so that the inner portion of the reaction container 35 is not contaminated by the bubble. Further, when an abnormality is detected at the sample suction operation, the reagent dispensing operation succeeded after the sample dispensing operation can be stopped, so that it can be prevented that a reagent is consumed without the correct sample discharging operation.

As described above, according to the present embodiment 1, the contamination of the reaction cell and the wasteful consumption of reagent can be prevented.

Further, in the present embodiment 1, the average of the pressure values, the maximum pressure value, the minimum pressure value, and their timings are took in as the feature variables at the constant timings based on the plunger operation start timing and the end timing as the first reference timing and the second reference timing respectively from the waveform of the discharging operation, the Statistical distance s D from the normal group data being compared with the threshold value, so that the dispensing failure can be correctly detected. The dispensing failure is caused by one part of the sample attached to the tip of the sample probe 15 bringing back the sample after the sample discharging operation. Therefore, an automatic analyzer capable for analyzing operation with high reliability can be provided.

(The Embodiment 2)

Figure 12:
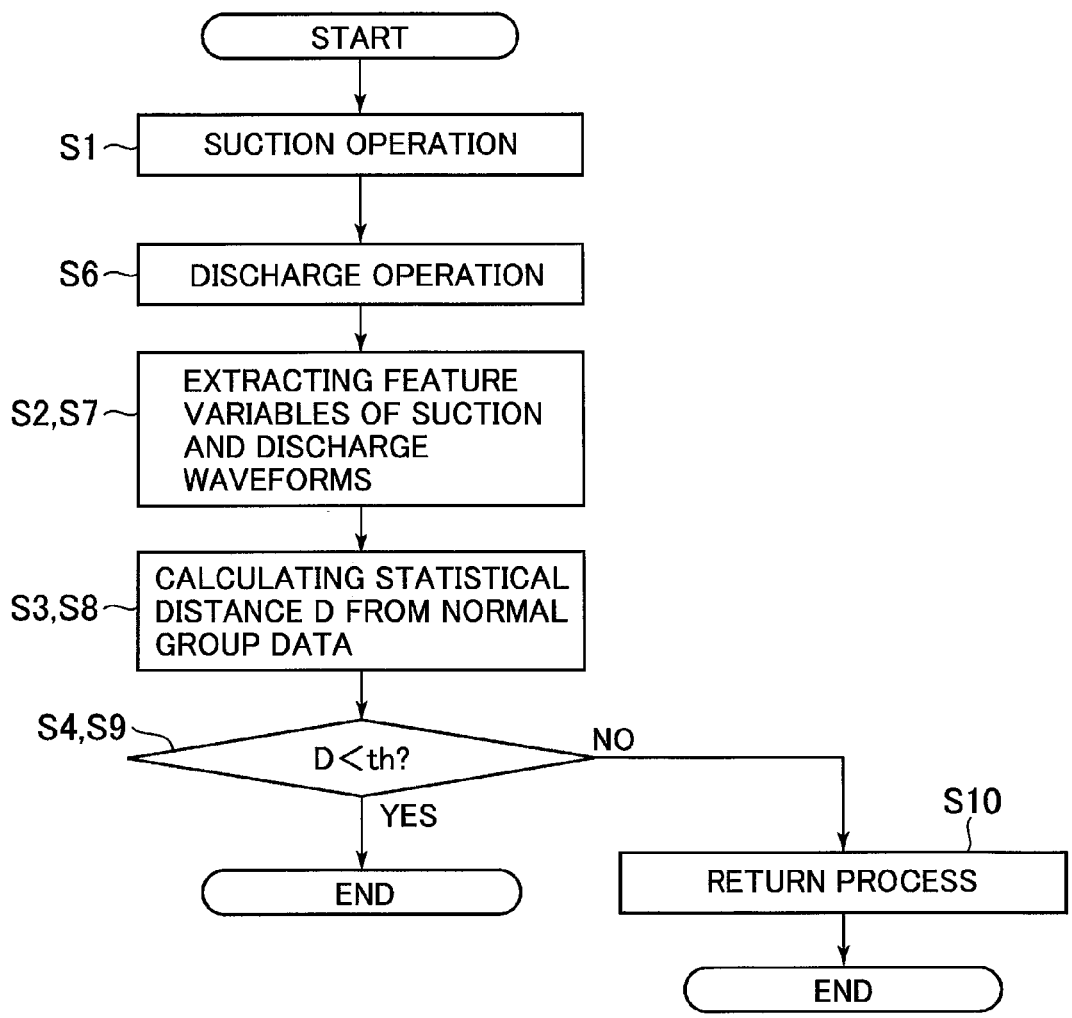
FIG. 12 is a flowchart of the judgment operation in the second embodiment of the present invention.

FIG. 12 is the flowchart of the discrimination operation of the embodiment 2 which is other embodiment of the present invention. The different point from the embodiment 1 is that the feature variables of both waveforms of the suction and discharge operations without separating the suction operation from the discharge operation after the discharging operation, and the threshold value th is compared with the calculated Statistical distance D from the normal group data. Other constructions are same as the embodiment 1, so that the detailed description and drawings are omitted. Further, the steps as same as the steps shown in FIG. 11 are designated by the same reference numerals in FIG. 12.

In FIG. 12, after the suction operation (the step S1) and the discharge operation (the step S6) are executed, the feature variables of the suction waveform and the discharge waveform being extracted (the steps S2 and step S7), the Statistical distance D from the normal group data being calculated (the steps S3 and S8). In this case, the statistical distance calculating unit 76a stores the suction waveform at the suction operation and the discharge waveform at the discharge operation into the memory 76b, reading out the waveforms from the memory 76b after the end of the discharge operation, executing the extraction of the feature variables and the calculation of the Statistical distance D.

Further, the return process is executed (the step S10) when the calculated Statistical distance D is larger than the threshold value. If the calculated Statistical distance D is smaller than the threshold value D, the process is finished.

In the present embodiment 2, since one time discrimination operation is executed by using both information of the suction operation and the discharge operation, the discrimination operation is not effected by noises easily, and an abnormality can be correctly discriminated without overlooking abnormalities at the suction operation and the discharge operation, and an automatic analyzer capable for executing the analysis operation with high reliability can be provided.

Namely, since the surface of liquid sample is being detected while the liquid sample is being sucked by the probe at the sucking operation in order to operate the probe to follow up the surface of the liquid, the mechanism operates to execute the above movement of the probe, so that it is highly possible to generate noises. On the other hand, the liquid surface follow-up movement of the probe is not required at the sample discharge operation, so that a little noise is generated at the sample discharge operation.

Further, when the D is smaller than the threshold value at both of the suction operation and the discharge operation, the operations are judged to be normal. When the D is larger than or equal to the threshold value at both of the suction operation and the discharge operation, the operations can be judged to be abnormal. When the D is larger than or equal to the threshold value at one of the suction operation and the discharge operation, it can be constructed that an abnormality or normality is judged in accordance with the difference between the D and the threshold value.

Further, in the present embodiment 2, the waveforms of the suction operation and the discharge operation are put together for one discrimination process, so that the discrimination operation can be simplified, and an automatic analyzer having high processing ability can be provided.

Further, in the present embodiment 2, the feature variables are extracted from both waveforms of the suction operation and the discharge operation, may being extracted from the waveform of one of the suction operation and the discharge operation. Further, fluctuation waveforms of the probe moving operation and the washing operation can be used.

(The Embodiment 3)

Figure 13:
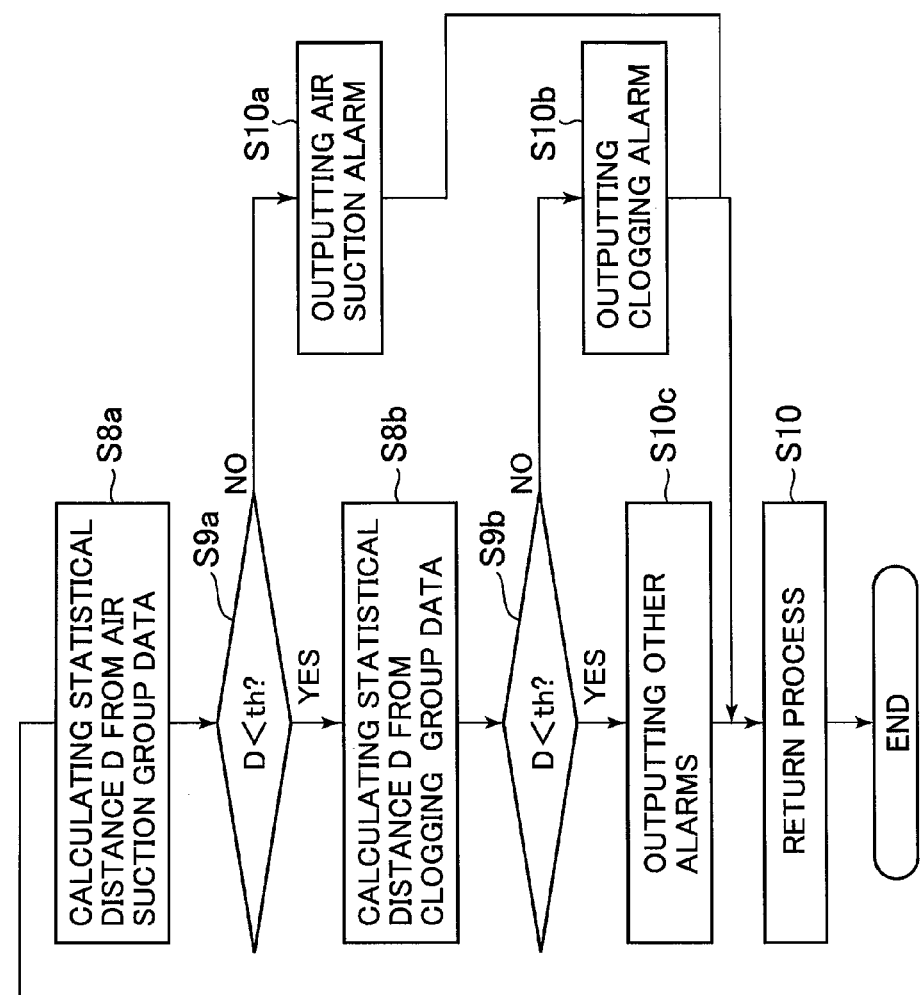
FIG. 13 is a flowchart of the judgment operation in the third embodiment of the present invention.
Figure 13:
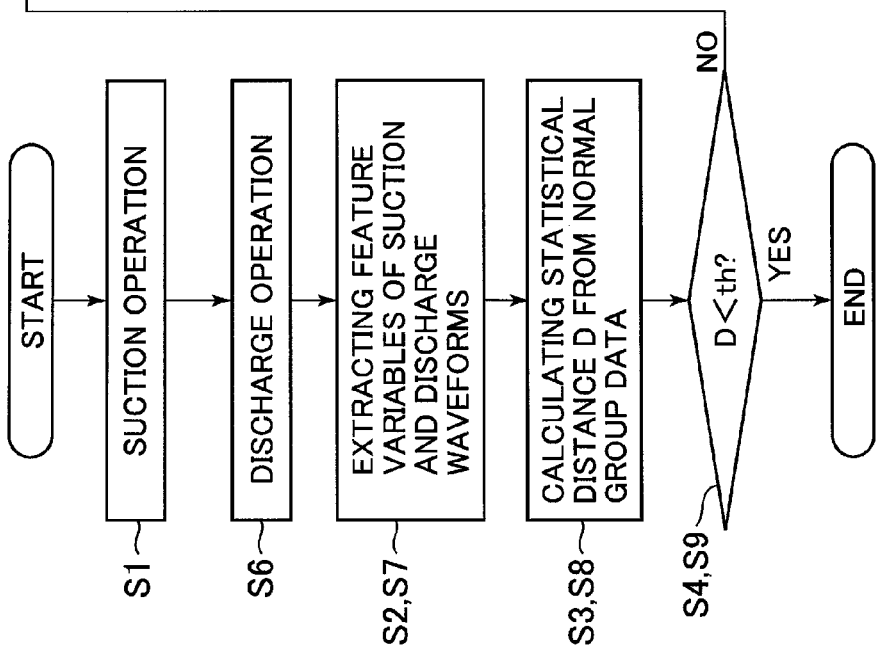

FIG. 13 is the flowchart of the discrimination operation of the embodiment 3 which is other embodiment of the present invention. The steps S1, S6, (S2, S7), (S3, S8), and (S4, S9) of the embodiment 3 are equal to the steps S1, S6, (S2, S7), (S3, S8), and (S4, S9) of the embodiment 2. The difference between the embodiment 3 and the embodiment 2 is that the cases of the occurrences of the air suction and the clogging are judged in the embodiment 3.

In the embodiment 3, the apparatus prepares not only normal group data but also the air suction occurrence group data and the clogging occurrence group data previously. Namely, the data are stored in the memory 76b.

The Statistical distance D between the feature variables extracted from the suction and discharge operations between the normal group data is calculated firstly (the steps S3 and S8). When it is judged that the calculated distance is more than or equal to the threshold value th (the steps S4 and S9), the Statistical distance calculation unit 76a further calculates the Statistical distance D from the air suction group data (the step S8a). It is judged whether or not the Statistical distance D is smaller than the threshold value th (the step S9a), and the air suction alarm is outputted when the D is smaller than the threshold value th (the step S10a), and the return process is executed (the step S10).

In the step S9a, when the D is more than or equal to the threshold value th, the Statistical distance D from the clogging group data is calculated further (the step S8b). It is judged whether or not the Statistical distance D is smaller than the threshold value th (the step S9b), and the clogging suction alarm is outputted when the D is smaller than the threshold value th (the step S10b), and the return process is executed (the step S10).

In the step S9b, when the D is more than or equal to the threshold value th, other alarm is outputted (the step S10c), the return process is executed (the step S10), and the discrimination operation is finished.

In the present embodiment 3, the apparatus can select suitable operation for each abnormality to judge not only the presence or absence of an abnormality but also the kind of the abnormality.

Further, the kinds of the abnormality as shown in the present embodiment 3 are the air suction operation and the clogging operation only. The present invention can deal with various kinds of abnormalities, such as an abnormal viscosity, a leakage of a flow passage, environment abnormal for example temperature or air pressure, an abnormal vibration, or the like.

Further, the present invention is not limited to judge the kinds of abnormalities, the degree of an abnormality can be represented quantitatively. One method for quantitatively representing the degree of an abnormality is to use the regression analysis using the feature variables as inputs, so that the apparatus can output the value of the viscosity of a sample, the assessed value of the discharge amount, for example.

DESCRIPTION OF REFERENCE NUMERALS

10 - - - Sample container, 12 - - - Sample disk, 15 - - - Sample probe, 20 - - - The first reagent probe, 21 - - - The second reagent probe, 24 - - - Dispensing flow passage, 25 - - - Quantitative pump, 26 - - - Presser sensor, 30 - - - Mixing apparatus, 35 - - - Reaction container, 36 - - - Reaction disk, 40 - - - Reagent container, 41 - - - The first reagent disk, 42 - - - The second reagent disk, 45 - - - Container washing mechanism, 50 - - - Light source, 51 - - - Spectrometer, 60 - - - Controller, 61 - - - Computer, 65 - - - Reduction part, 66 - - - Plunger, 67 - - - Drive mechanism, 68 - - - Valve, 69 - - - Pump, 75 - - - A/D converter, 76 - - - Signal processor, 77 - - - System liquid, 78 - - - Separate air, 79 - - - Suction solution

The invention claimed is:

1. An automatic analyzer comprising:
a dispensing mechanism including a dispensing probe for dispensing a sample or a reagent into a reaction container;
a quantitative pump for sucking and discharging the sample or the reagent quantitatively through the dispensing probe, the quantitative pump being driven during a plurality of different periods of time, each beginning at a drive start time and ending at a drive end time, and each time period corresponding to an amount of a sample or a reagent being sucked or discharged;
an analysis part for analyzing a sample in the reaction container;
a pressure sensor for detecting a pressure in the probe; and
a signal processing unit, having a memory, and programmed to:
extract feature variables from pressure data detected by the pressure sensor at a dispensing operation of the dispensing probe based on a first reference time which is the drive start time for driving the quantitative pump at the dispensing operation of the dispensing probe;
extract feature variables from pressure data detected by the pressure sensor at the dispensing operation of the dispensing probe based on a second reference time which is the drive end time for driving the quantitative pump at the dispensing operation of the dispensing probe;
calculate a statistical distance between predetermined common reference pressure fluctuation data, that is stored in the memory, and the feature variables regardless of the amount of sample or reagent; and
judge whether or not the dispensing operation of the dispensing probe is correctly executed based on whether or not the calculated statistical distance is lower than a constant threshold value,
wherein the reference pressure fluctuation data stored in the memory of the signal processing unit are plural kinds of reference pressure fluctuation data whose dispensing conditions, including an amount of sample or reagent, are different from one another.

2. The automatic analyzer according to claim 1, wherein the statistical distance calculated by the signal processing unit is one of a Mahalanobis distance, a Euclidean distance, a Chebychev distance, a Multi variate normal density, and a Minkowski distance.

3. The automatic analyzer according to claim 1, wherein the signal processing unit judges whether or not a dispensing operation is correctly executed by using both of pressure data of the dispensing probe sucking operation and discharging operation of sample or reagent.

4. The automatic analyzer according to claim 1, wherein the reference pressure fluctuation data is data of a pressure waveform obtained by dispensing a liquid whose viscosity has a viscosity range substantially equal to a viscosity range of a normal sample or a normal reagent.

5. The automatic analyzer according to claim 1, wherein the signal processing unit uses abnormal group pressure data caused by a specific reason as the reference pressure fluctuation data, discriminating a kind of an abnormality, when the signal processing unit judges that the dispensing probe could not execute a dispensing operation correctly.

6. A method for judging whether a dispensing operation of an automatic analyzer is normal or abnormal, the automatic analyzer having a dispensing mechanism including a dispensing probe for dispensing a sample or a reagent into a reaction container and a quantitative pump for sucking and discharging the sample or the reagent quantitatively through the dispensing probe, the quantitative pump being driven during a plurality of different periods of time, each beginning at a drive start time and ending at a drive end time, and each time period corresponding to an amount of a sample or a reagent being sucked or discharged, an analysis part for analyzing a sample in the reaction container, and a pressure sensor for detecting a pressure in the probe, the method comprising the steps of:
extracting feature variables from pressure data detected by the pressure sensor at a dispensing operation of the dispensing probe based on a first reference time which is the drive start time for driving the quantitative pump at the dispensing operation of the dispensing probe;
extracting feature variables from pressure data detected by the pressure sensor at the dispensing operation of the dispensing probe based on a second reference time which is the drive end time for driving the quantitative pump at the dispensing operation of the dispensing probe;
calculating a statistical distance between predetermined common reference pressure fluctuation data and the feature variables regardless of the amount of sample or reagent; and
judging whether or not the dispensing operation of the dispensing probe is correctly executed based on whether or not the calculated statistical distance is lower than a constant threshold value, wherein the reference pressure fluctuation data of the signal processing unit are plural kinds of reference pressure fluctuation data whose dispensing conditions, including an amount of sample or reagent, are different from one another.

7. The method for judging normal or abnormal of a dispensing operation of an automatic analyzer according to claim 6, wherein the statistical distance to be calculated is one of a Mahalanobis distance, a Euclidean distance, a Chebychev distance, a Multi variate normal density, and a Minkowski distance.

8. The method for judging normal or abnormal of a dispensing operation of an automatic analyzer according to claim 6, wherein whether or not a dispensing operation is correctly executed is judged by using both of pressure data of the dispensing probe sucking operation and discharging operation of sample or reagent.

9. The method for judging normal or abnormal of a dispensing operation of an automatic analyzer according to claim 6, wherein the reference pressure fluctuation data is data of a pressure waveform obtained by dispensing a liquid whose viscosity has a viscosity range substantially equal to a viscosity range of a normal sample or a normal reagent.

10. The method for judging normal or abnormal of a dispensing operation of an automatic analyzer according to claim 6, wherein abnormal group pressure data caused by specific reason are used as the reference pressure fluctuation data, and a kind of an abnormality is discriminated when the signal processing unit judges that the dispensing probe could not execute a dispensing operation correctly.

11. The automatic analyzer according to claim 1, wherein the feature variables include:

pressure values at constant timings based on the first reference time, a time elapsed from the first reference time to a first occurrence of a maximum or a minimum pressure fluctuation, a pressure value of the maximum or minimum pressure fluctuation from the first reference time, pressure values at constant timing based on the second reference time, a time elapsed from the second reference time to a first occurrence of a maximum or a minimum pressure fluctuation, and a pressure value of the maximum or minimum pressure fluctuation from the second reference time.

12. The method according to claim 6, wherein the feature variables include:

pressure values at constant timings based on the first reference time, a time elapsed from the first reference time to a first occurrence of a maximum or a minimum pressure fluctuation, a pressure value of the maximum or minimum pressure fluctuation from the first reference time, pressure values at constant timing based on the second reference time, a time elapsed from the second reference time to a first occurrence of a maximum or a minimum pressure fluctuation, and a pressure value of the maximum or minimum pressure fluctuation from the second reference time.

13. The automatic analyzer according to claim 1, wherein the feature variables extracted based on the first reference time are average values of the pressure data at a constant time interval before and after the first reference time and the feature variables extracted based on the second reference time are average values of the pressure data at a constant time interval before and after the second reference time.

14. The method for judging whether a dispensing operation of an automatic analyzer is normal or abnormal according to claim 6, wherein the feature variables extracted based on the first reference time are average values of the pressure data at a constant time interval before and after the first reference time and the feature variables extracted based on the second reference time are average values of the pressure data at a constant time interval before and after the second reference time.

* * * * *